United States Patent
Pahlevan et al.

(10) Patent No.: US 9,622,666 B2
(45) Date of Patent: Apr. 18, 2017

(54) NONINVASIVE SYSTEMS FOR BLOOD PRESSURE MEASUREMENT IN ARTERIES

(71) Applicant: California Institute of Technology, Pasadena, CA (US)

(72) Inventors: Niema Pahlevan, Woodland Hills, CA (US); Morteza Gharib, Altadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 695 days.

(21) Appl. No.: 13/715,743

(22) Filed: Dec. 14, 2012

(65) Prior Publication Data

US 2013/0178736 A1    Jul. 11, 2013

Related U.S. Application Data

(60) Provisional application No. 61/570,711, filed on Dec. 14, 2011.

(51) Int. Cl.
| | |
|---|---|
| *A61B 5/021* | (2006.01) |
| *A61B 5/05* | (2006.01) |
| *A61B 8/04* | (2006.01) |
| *A61B 5/02* | (2006.01) |
| *A61B 8/06* | (2006.01) |
| *A61B 8/00* | (2006.01) |
| *A61B 8/08* | (2006.01) |

(52) U.S. Cl.
CPC ............ *A61B 5/021* (2013.01); *A61B 5/0507* (2013.01); *A61B 8/04* (2013.01); *A61B 8/5223* (2013.01); *A61B 5/02007* (2013.01); *A61B 8/06* (2013.01); *A61B 8/4427* (2013.01); *A61B 8/485* (2013.01)

(58) Field of Classification Search
CPC ....... A61B 8/04; A61B 8/05223; A61B 8/006; A61B 8/04427; A61B 8/0485; A61B 5/021; A61B 5/0507; A61B 5/02007
See application file for complete search history.

(56) References Cited

U.S. PATENT DOCUMENTS

| | | | |
|---|---|---|---|
| 4,669,485 A | * | 6/1987 | Russell .................. A61B 5/021 600/492 |
| 4,933,545 A | | 6/1990 | Saaski et al. |
| 4,991,197 A | | 2/1991 | Morris |

(Continued)

FOREIGN PATENT DOCUMENTS

| | | |
|---|---|---|
| EP | 1279370 A1 | 1/2003 |
| JP | 2002-065677 | 3/2002 |

(Continued)

OTHER PUBLICATIONS

Of Stoner et al., Relationship between blood velocity and conduit artery diameter and the effects of smoking on vascular responsiveness, J Appl Physiol 96: 2139-2145, 2004.*

(Continued)

*Primary Examiner* — Bo J Peng
(74) *Attorney, Agent, or Firm* — One LLP

(57) ABSTRACT

Hardware and software methodology are described for a non-invasive approach to blood pressure measurement in pulmonary artery and systemic arteries by using wall displacement and blood velocity that are measured using ultrasound, microwave techniques and/or other radiofrequency (RF) techniques.

5 Claims, 1 Drawing Sheet

(56) References Cited

U.S. PATENT DOCUMENTS

| | | | |
|---|---|---|---|
| 5,086,776 A | | 2/1992 | Fowler, Jr. et al. |
| 5,146,083 A | | 9/1992 | Zuckerwar et al. |
| 5,265,615 A | | 11/1993 | Frank et al. |
| 5,309,916 A | * | 5/1994 | Hatschek ...................... 600/485 |
| 5,411,028 A | * | 5/1995 | Bonnefous ......... A61B 5/02007 |
| | | | 600/438 |
| 6,135,957 A | | 10/2000 | Cohen-Bacrie et al. |
| 6,477,406 B1 | | 11/2002 | Turcott |
| 6,483,929 B1 | | 11/2002 | Murakami et al. |
| 6,491,647 B1 | | 12/2002 | Bridger et al. |
| 6,676,608 B1 | | 1/2004 | Keren |
| 6,738,734 B1 | | 5/2004 | Huang |
| 7,272,431 B2 | | 9/2007 | McGrath |
| 7,811,234 B2 | | 10/2010 | McGrath |
| 7,889,053 B2 | | 2/2011 | McGrath et al. |
| 8,033,996 B2 | | 10/2011 | Behar |
| 8,232,866 B2 | | 7/2012 | McGrath et al. |
| 8,435,181 B2 | | 5/2013 | Yang et al. |
| 9,026,193 B2 | | 5/2015 | Pahlevan et al. |
| 2003/0069508 A1 | | 4/2003 | Kawaguchi et al. |
| 2003/0135124 A1 | * | 7/2003 | Russell ......................... 600/500 |
| 2003/0191400 A1 | | 10/2003 | Shalman et al. |
| 2004/0088123 A1 | * | 5/2004 | Ji ..................................... 702/45 |
| 2005/0143667 A1 | | 6/2005 | Park et al. |
| 2007/0016031 A1 | * | 1/2007 | Mourad ............... A61B 5/0048 |
| | | | 600/437 |
| 2007/0185391 A1 | | 8/2007 | Morgan |
| 2007/0210786 A1 | | 9/2007 | Allen et al. |
| 2007/0238995 A1 | | 10/2007 | Sui et al. |
| 2008/0234568 A1 | | 9/2008 | Ouchi |
| 2009/0018422 A1 | | 1/2009 | Banet et al. |
| 2009/0204012 A1 | | 8/2009 | Joeken |
| 2010/0185084 A1 | | 7/2010 | Zhang |
| 2011/0040181 A1 | | 2/2011 | Yokota et al. |
| 2011/0130800 A1 | | 6/2011 | Weinstein et al. |
| 2011/0224529 A1 | | 9/2011 | Lading |
| 2011/0275936 A1 | | 11/2011 | Cho et al. |
| 2012/0143068 A1 | | 6/2012 | Cheng et al. |
| 2012/0146796 A1 | | 6/2012 | Margon et al. |
| 2012/0238834 A1 | | 9/2012 | Hornick |
| 2012/0289848 A1 | | 11/2012 | Li et al. |
| 2013/0078095 A1 | | 3/2013 | Olesen |
| 2013/0172723 A1 | | 7/2013 | Baxi et al. |
| 2013/0184573 A1 | | 7/2013 | Pahlevan et al. |
| 2014/0073969 A1 | | 3/2014 | Zou et al. |

FOREIGN PATENT DOCUMENTS

| | | |
|---|---|---|
| KR | 10-2002-0055362 | 7/2002 |
| KR | 10-2003-0070315 | 8/2003 |
| KR | 10-2006-0004931 | 1/2006 |
| WO | WO 2012/011029 | 1/2012 |

OTHER PUBLICATIONS

WO, PCT/US2012/069947 IPRP, Jun. 17, 2014.
WO, PCT/US2012/071452 IPRP, Jun. 24, 2014.
Abbas, A. E. et al., Echocardiographic Determination of Mean Pulmonary Artery Pressure, The American Journal of Cardiology, vol. 92, Dec. 1, 2003.
Angtuaco, M. J. et al., Noninvasive Estimation of Diastolic Pulmonary Artery Pressure by Doppler Analysis of Tricuspid Regurgitation Velocity in Pediatric Patients, Congent. Heart Dis. 2011.
Cremer, A. et al., Determination of central blood pressure by a noninvasive method (brachial BP and QKD interval), Journal of Hypertension, vol. 30, No. 00, 2012.
Friedberg, M. K. et al., A Novel Eschocardiographic Doppler Method for Estimatin of Pulmonary Arterial Pressures, Journal of the American Society of Echocardiography, May 2006.
Greenfield, Jr., J. C. et al., Relation between pressure and diameter in main pulmonary artery of man, J. Appl. Physiol. 18(3):557-559 (1963).
US, PCT/US2012/069947 ISR/Written Opinion, Feb. 27, 2013.
Lanzarini, L. et al., Noninvasive estimation of both systolic and diastolic pulmonary artery pressure from Doppler analysis of tricuspid regurgitant velocity spectrum in patients with chronic heart failure, American Heart Journal, Dec. 2002.
Lee, J. Y. et al., A Microprocessor-Based Noninvasive Arterial Pulse Wave Analyzer, IEEE Transactions on Biomedical Engineering, vol. BME-32, No. 6, Jun. 1985.
Milan, A. et al., Echocardiographic Indexes for the Non-Invasive Evaluation of Pulmonary Hemodynamics, Journal of the American Society of Echocardiography, vol. 23, No. 3, Mar. 2010.
Patel, D. J. et al., Mechanical properties and dimensions of the major pulmonary arteries, J. Appl. Physiol. 15(1):92-96 (1960).
Selton-Suty, C. et al., Non-invasive investigations of the right heart: How and why?, Archives of Cardiovascular Disease (2009) 102, 219-232.
Daubechies, I., "The Wavelet Transform, Time-Frequency Localization and Signal Analysis", IEEE Transactions on Information Theory, 1990, vol. 36, No. 5, pp. 961-1005.
Denardo, S.J., et al., "Pulse Wave Analysis of the Aortic Pressure Waveform in Severe Left Ventricular Systolic Dysfunction", Circ Heart Fail, 2010, vol. 3, pp. 149-156.
Feng, J., et al., "Determination of wave speed and wave separation in the arteries using diameter and velocity", Journal of Biomechanics, 2010, vol. 43, pp. 455-462.
Fletcher, R. R., et al., "Clip-on wireless wearable microwave sensor for ambulatory cardiac monitoring", IEEE, 2010, pp. 365-369.
Hou, T.Y. et al., "Adaptive Data Analysis Via Sparse Time-Frequency Representation", Advances in Adaptive Data Analysis, 2011, vol. 3, Nos. 1 & 2, pp. 1-28.
WO, PCT/US2012/071452 ISR, Mar. 14, 2013.
WO, PCT/US2013/053068 ISR, Nov. 26, 2013.
WO, PCT/US2013/054529 ISR, Nov. 27, 2013.
Hou, T.Y. et al., "Data-driven time-frequency analysis", Appl. Comput, Harman. Anal., 2013, vol. 35, pp. 284-308.
Huang, N.E., et al., "The empirical mode decomposition and the Hilbert spectrum for nonlinear and non-stationary time series analysis", Proc. R. Soc. Lond. A, 1998, vol. 454, pp. 903-995.
Huang, W., et al., "Use of intrinsic modes in biology: Examples of indicial response of pulmonary blood pressure to ± step hypoxia", Proc. Natl. Acad. Sci. USA, 1998, vol. 95, pp. 12766-12771.
Pahlevan, N.M., et al., "A Physiologically Relevant, Simple Outflow Boundary Model for Truncated Vasculature", Annals of Biomedical Engineering, 2011, vol. 39, No. 5, pp. 1470-1481.
Pahlevan, N.M., et al., "Low pulse pressure with high pulsatile external left ventricular power: Influence of aortic waves", Journal of Biomechanics, 2011, vol. 44, No. 11, pp. 2083-2089.
Pahlevan, N.M., et al., "Aortic Wave Dynamics and Its Influence on Left Ventricular Workload", PLoS ONE, 2011, vol. 6, No. 8, pp. 1-8.
Pahlevan, N.M., et al., "A Bio-Inspired Approach for the Reduction of Left Ventricular Workload", PLoS ONE, 2014, vol. 9, No. 1, pp. 1-12.
Pahlevan, N.M., et al., "Intrinsic frequency for a systems approach to haemodynamic waveform analysis with clinical applications", Journal of the Royal Society Interface, 2014, vol. 11, pp. 1-10.
WO, PCT/US2014/061256 ISR, Jan. 22, 2015.
WO, PCT/US2013/053068 IPRP, Feb. 3, 2015.
WO, PCT/US2013/054529 IPRP, Feb. 17, 2015.
WO, PCT/US2015/012293 ISR, Apr. 30, 2015.
WO, PCT/US2015/012096 ISR and Written Opinion, Jun. 29, 2015.
Yokobori, Jr., A. T., et al., "The Analysis and Diagnosis of Unstable Behavior of the Blood Vessel Wall with an Aneurysm Based on Noise Science", Journal of Atherosclerosis and Thrombosis, 2006, vol. 13, No. 4, pp. 163-174.
U.S. Appl. No. 13/964,631 Office Action, Jan. 21, 2016.
Hassan, S., et al., "Systolic time intervals: a review of the method in the non-invasive investigation of cardiac function in health, disease and clinical pharmacology", Postgraduate Medical Journal, 1983, vol. 59, pp. 423-434.
Heckman, J. L., et al., "Frequency analysis approach to the origin of the first and second heart sounds", American Heart Journal, 1982, vol. 104, pp. 1309-1318.
Wikipedia, Cardiac cycle, published Nov. 14, 2012.

(56) References Cited

OTHER PUBLICATIONS

U.S. Appl. No. 15/006,926 Non-Final Office Action, May 4, 2016.
U.S. Appl. No. 14/601,170 Non-Final Office Action, May 5, 2016.
WO, PCT/US2014/061256 IPRP, Apr. 19, 2016.
Harada, A., et al., "Development of a Non-invasive Real-time Measurement System of Wave Intensity", IEEE Ultrasonics Symposium, 2000, pp. 1517-1520.
Khir, A. W., et al., "Wave intensity I the ascending aorta: effects of arterial occlusion", Journal of Biomechanics, 2005, vol. 38, pp. 647-655.
Sugawara, M., et al., "Clinical usefulness of wave intensity analysis", Med. Biol. Eng. Comput., 2009, vol. 47, pp. 197-206.
Swillens, A., et al., "Effect of an Abdominal Aortic Aneurysm on Wave Reflection in the Aorta", IEEE Transactions on Biomedical Engineering, 2008, vol. 55, No. 5, pp. 1602-1611.
Van Den Wijngaard, J. P.H.M., et al., "Comparison of arterial waves derived by classical wave separation and wave intensity analysis in a model of aortic coarctation", Med. Biol. Eng. Comput., 2009, vol. 47, pp. 211-220.
EP, 13829710.6 Extended Search Report, Mar. 1, 2016.

\* cited by examiner

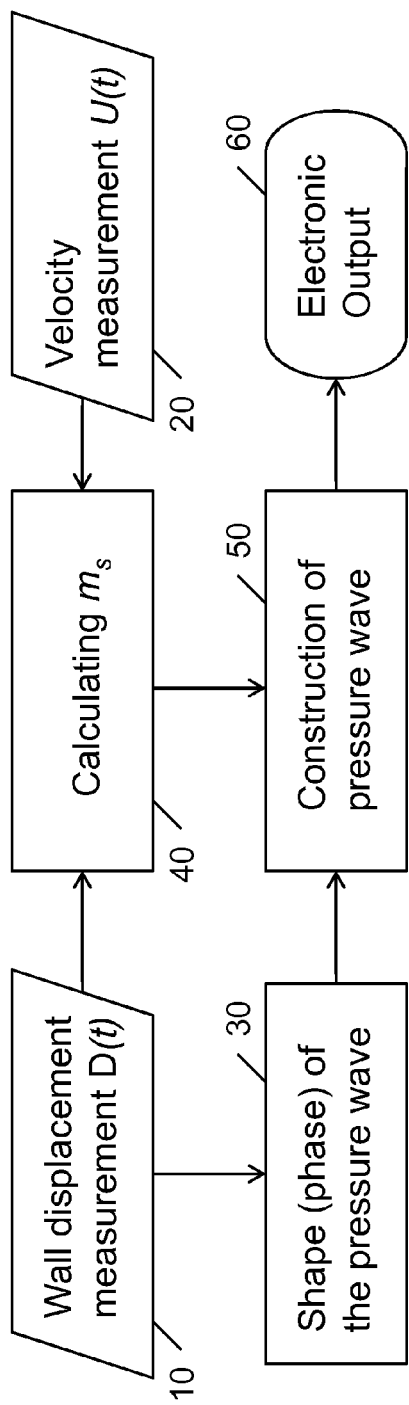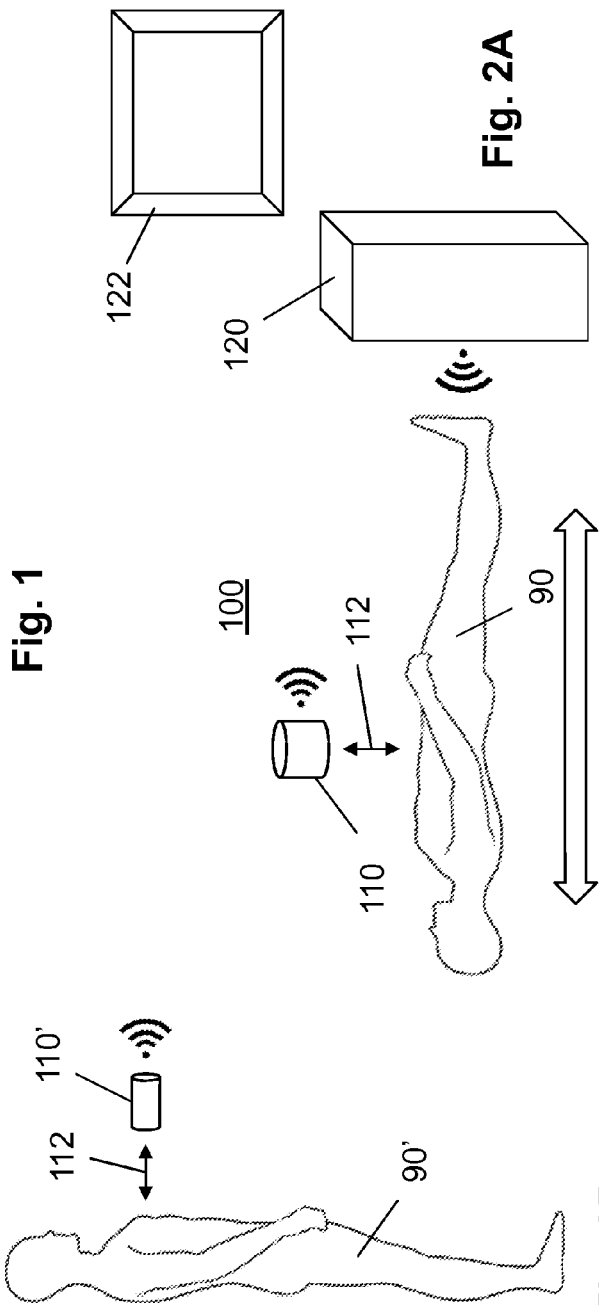

NONINVASIVE SYSTEMS FOR BLOOD PRESSURE MEASUREMENT IN ARTERIES

RELATED APPLICATIONS

This filing claims the benefit of U.S. Provisional Patent Application Ser. No. 61/570,711 filed Dec. 14, 2011 and entitled, "Noninvasive Method and Device for Measurement of Instantaneous Pressure in Arteries," incorporated by reference herein in its entirety for all purposes.

FIELD

This filing relates to non-invasive blood pressure measurement.

BACKGROUND

The pulmonary and systemic arterial pressure wave is an important parameter in the diagnosis of various pulmonary artery and systemic artery diseases such as pulmonary hypertension, pulmonary stenosis, systemic hypertension and arterial stenosis. Invasive methods of pressure measurement cause discomfort for the patients, and they include procedural and post-operative risks, the later including infection with an increasing incidence of mortality due to antibiotic resistant bacteria. Accordingly, non-invasive techniques for blood pressure measurement are preferred and may become increasingly important.

Once such technique is known as applanation tonometry. However, it is limited to measurement in certain locations such as the radial arteries at wrist or carotid arteries where these systemic arteries are close to the surface of the skin. Moreover, commercially-available tonometric devices are all quite motion-sensitive further limiting their use/applicability. Still further: affixing, wearing and ultimately removing the force or displacement sensor employed a tonometric monitoring system can be difficult and sometimes uncomfortable.

Another technique for estimating blood pressure is variously described in which blood velocity is measured via ultrasound Doppler and then the Bernoulli equation applied to calculate a result. However, the Bernoulli equation does not properly apply to moving boundary condition systems or those involving unsteady flow—both of which are features of the relevant biological systems. As such, the accuracy/applicability of these approaches are limited. These methods can only provide estimates for mean pressure, systolic pressure, and/or diastolic pressure. They are not able to provide the pressure wave or pressure at any time during a cardiac cycle.

Therefore, improved noninvasive techniques—especially noncontact methods—for measuring and/or monitoring the arterial pressure waveform are needed.

SUMMARY

The inventive embodiments include the subject devices and systems (e.g., including the sensor hardware referenced herein and the addition of a computer processor and other ancillary or support electronics and various housing elements), and methods (including the hardware and software for carrying out the same). These embodiments provide a noninvasive approach for blood pressure measurement in pulmonary artery and systemic arteries by using wall displacement and blood velocity that are measured non-invasively using ultrasound and/or microwave or other radiofrequency (RF) techniques. Methods, devices, and systems are provided for calculating instantaneous pressure in the arteries and/or outputting highly accurate pressure wave estimates generated from a calculated slope of the D-U loop (as defined below) together with vessel wall displacement wave measurements.

BRIEF DESCRIPTION OF THE DRAWINGS

The figures provided herein are diagrammatic and not necessarily drawn to scale, with some components and features exaggerated and/or abstracted for clarity. Variations from the embodiments pictured are contemplated. Accordingly, depiction of aspects and elements in the figures are not intended to limit the scope of the claims, except when such intent is explicitly stated as such.

FIG. 1 is a flowchart illustrating activity in an example embodiment of the subject method.

FIGS. 2A-B illustrate options for systems operating according to an example embodiment of the subject method.

DETAILED DESCRIPTION

Various example embodiments are described below. Reference is made to these examples in a non-limiting sense. They are provided to illustrate more broadly applicable aspects of inventive aspects. Various changes may be made to the embodiments described and equivalents may be substituted without departing from their true spirit and scope. In addition, many modifications may be made to adapt a particular situation, material, composition of matter, process, process act(s) or step(s) to the objective(s), spirit or scope of the claims made herein.

That said, the subject technique is based on the fact that the walls of the large central pulmonary and systemic arteries are almost elastic. Therefore, the blood pressure and their wall displacement wave can be characterized as having the same shape. Stated another way, the wall displacement wave is in phase with the blood pressure wave.

Thus, in the absence of a reflected wave at the beginning of the cardiac cycle, the below relation between an increment of pressure (dP) and an increment of average velocity over cross-section area (dU) holds:

$$dP_+ = (\rho c) dU_+ \quad (1)$$

where $\rho$ is the density of fluid, c is the wave speed, and "+" sign corresponds to forward waves. In addition from 1D wave theory, wave speed can be written as a function of blood vessel distensibility (dis):

$$c = \sqrt{\frac{1}{\rho \cdot dis}} \quad (2)$$

where dis can be calculated as:

$$dis = \frac{1}{A} \frac{dA}{dP} \quad (3)$$

where A is the cross-section area, $A = \pi/4 \cdot D^2$, and D is the diameter of the vessel. Using the chain rule and substituting D in (3) results in:

$$dis = \frac{2}{D}\frac{dD}{dP}. \quad (4)$$

Combining (4) and (2) and substitute in (1) yields:

$$dD_+ = \left(\frac{D}{2c}\right)dU_+. \quad (5)$$

Accordingly, the slope of a graph of the vessel diameter plotted against blood velocity, generally center-line blood or cross-section area average of the velocity, (i.e., the D-U graph or loop) at the beginning of the cardiac cycle ($m_s$) is equal to D/2c.

Also, wall displacement wave speed is related to Young's modulus (E) and wall thickness (t) through Moens-Kortweg equation:

$$c = \sqrt{\frac{Eh}{\rho D}} \rightarrow Eh \quad (6)$$
$$= \rho Dc^2.$$

Using thin elastic tube theory with applied internal pressure, the following equation holds:

$$\sigma_{\theta\theta} = \frac{PR}{h} \quad (7)$$

where $\sigma_{\theta\theta}$ is the circumferential stress, R is the radius of the tube P is the internal pressure, and h is the thickness of the tube. Assuming that radial stress is much smaller than circumferential stress and by using (7) the circumferential strain can be written as:

$$\varepsilon_{\theta\theta} = \frac{PR}{Eh}. \quad (8)$$

Based on the definition of the circumferential strain:

$$\varepsilon_{\theta\theta} = \frac{\Delta R}{R} \quad (9)$$

and combining (8) and (9), replacing diameter for radius yields:

$$Eh = \frac{PD^2}{2(\Delta D)}. \quad (10)$$

Substituting Eh from (10) into (6) results in:

$$c = \sqrt{\frac{PD}{2\rho(\Delta D)}}. \quad (11)$$

From equation (5) the slope of D-U graph at the beginning of the cardiac cycle is $$m_s = \frac{dD_+}{dU_+} \quad (12)$$
$$= \frac{D}{2c}.$$

Combining (11) and (12) and solving for P yields:

$$P = \frac{\rho D(\Delta D)}{2m_s^2} \quad (13)$$

where $D_0$ for $\Delta D$ (i.e., $D-D_0$) may be determined by of any of a variety of approaches as typical in the art. For instance, any of a search algorithm, allometric equations (age-corrected), diastolic diameter, clinically derived values, or an approximate based on patient history may be employed.

With these principles in mind, FIG. 1 shows the steps for noninvasive instantaneous pressure measurement. At 10 and 20, wall displacement and velocity waves are measured noninvasively at the same or substantially the same location (e.g., within about 1 cm for large/larger vessels and within about 5 mm in small/smaller vessels and more generally—though not necessarily—within +/−1 vessel diameter in separation) along any pulmonary or systemic artery using ultrasound, microwave, or other suitable technique(s). These measurements are accomplished with at least one sensor adapted to record a first data set that correlates to blood vessel distension and adapted to record a second data set that correlates to blood velocity, more particularly center-line blood velocity or cross-sectional area average of the velocity. Then at least one computer processor is programmed to convert the first data set to a measurement of blood vessel distention and the second data set to a measurement of relevant blood velocity.

At 30, the shape of the pressure wave is captured or recorded and will be the same as the shape of the wall displacement (assuming a linear elastic vessel wall) measured at 10.

At 40, the D-U loop is determined and the slope ($m_s$) at the beginning of a cardiac cycle calculated therefrom. Or the slope may be calculated in another fashion. In any case, with $m_s$, the pressure may be calculated at any moment during the cardiac cycle using equation (13) or any similar equation. At 50, the blood pressure wave, if desired, is so-constructed.

A highly accurate estimate (given the assumptions noted above) of blood pressure is thus determined from the shape and magnitude calculated at 30 and 40. Any (or all) such data (e.g., instantaneous pressure, systolic/diastolic max/min pressure, pulse pressure, and/or the entire pressure wave) is output at 60 in a computer-readable format or data stream. This data can be in the form of an average over a given number of cycles or as a real time data stream. Accordingly, instantaneous pressure measurements and/or the calculated pressure wave may be displayed in real time for physician evaluation and/or logged for monitoring or subsequent evaluation of a physician, or other analysis.

Regardless, what is meant by "real time" in the context above will generally mean that it takes about 1 second or less from the time of data acquisition for calculation and data presentation, more often such action is essentially without the delay perceptible to humans. In any case, real time activity in the subject embodiments concern manipulation of such a mass of data and calculations that the task is well beyond human capacity, thereby requiring the use of a computer processor.

FIG. 2A diagrammatically illustrates such a computer-based system 100 with various hardware and patient-handling options. Namely, a patient may be scanned in a supine position 90, in a standing position 90' or otherwise. The scanner 110 may be associated with an armature, a C-arm, a scanner "tunnel," or otherwise configured. If scanner 110' is configured as a handheld scanner, then a standing position 90' may be preferable to accommodate the handheld operation as shown in FIG. 2B. The scanner may be moved relative to the patient to scan a selected area or areas. Or the patient may be moved relative to the scanner (as indicated). Notably, targeting larger central vessels (as opposed to smaller more distal vessels) may be desirable for improved accuracy. In the larger vessels, diameter displacements are generally larger. Also, the assumption of vessel elasticity is more perfect/pure, whereas peripheral vessels tend to exhibit a greater degree of visco-elastic behavior. Still, in most any location selected the subject embodiments offer useful improvement over previous techniques.

In any case, scanner 110/110' includes on-board electronics for sending and receiving signals 112 to perform the referenced measurements of blood flow velocity and/or vessel distension. Use of microwave sensor (at least for measuring vessel displacement) and/or ultrasound sensors (for measuring either or both vessel distension and blood velocity) for such purposes is well known. An example of suitable publicly-available hardware includes the GE LOGIQ Book Portable Ultrasound Machine, which technology is readily adapted to the subject methods and systems.

Alternatively, a hand-held scanner 110 incorporated in system 100 may advantageously be battery-powered so as to avoid connection to a wall socket. Whether hand-held or incorporated or in a larger unity, the scanner device(s) may interface by wireless (as indicated) or wired (not shown) communication with a general purpose computer 120, optionally including display 122 to perform and communicate results, respectively. Otherwise, on-board processing and/or display hardware may be provided in connection with the sensor housing itself. Such options would be especially useful for a hand-held or semi-portable device as these may be used by a patient/subject at home, during travel, etc.

Variations

In addition to the embodiments that been disclosed in detail above, still more are possible within the classes described and the inventors intend these to be encompassed within this Specification and claims. This disclosure is intended to be exemplary, and the claims are intended to cover any modification or alternative which might be predictable to a person having ordinary skill in the art.

Moreover, the various illustrative processes described in connection with the embodiments herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has a user interface port that communicates with a user interface, and which receives commands entered by a user, has at least one memory (e.g., hard drive or other comparable storage, and random access memory) that stores electronic information including a program that operates under control of the processor and with communication via the user interface port, and a video output that produces its output via any kind of video output format, e.g., VGA, DVI, HDMI, DisplayPort, or any other form.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein. The camera may be a digital camera of any type including those using CMOS, CCD or other digital image capture technology.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software, the functions may be stored on, transmitted over or resulting analysis/calculation data output as one or more instructions, code or other information on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and BLU-RAY disc where disks usually reproduce data magnetically, while discs reproduce data optically with lasers. Combinations of the above should also be included within the scope of computer-readable media.

Operations as described herein can be carried out on or over a website. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

Also, the inventors intend that only those claims which use the words "means for" are intended to be interpreted under 35 USC 112, sixth paragraph. Moreover, no limitations from the specification are intended to be read into any claims, unless those limitations are expressly included in the claims. The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, it is contemplated that any optional feature of the embodiment variations described may be set forth and claimed independently, or in combination with any one or more of the features described herein. Reference to a singular item, includes the possibility that there is a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

The breadth of the present inventive subject matter is not to be limited to the examples provided and/or the subject specification, but rather only by the scope of the claim language. All references cited are incorporated by reference in their entirety. Although the foregoing embodiments been described in detail for purposes of clarity of understanding, it is contemplated that certain modifications may be practiced within the scope of the appended claims.

The invention claimed is:

1. A method of blood pressure estimation of a human patient, the method comprising:
   selecting a blood vessel;
   measuring blood vessel distension and blood velocity with at least one sensor;
   calculating, in real time, an average blood pressure over a number of cycles based on the measured blood vessel distension and the measured blood velocity using a slope calculated for vessel diameter plotted against the measured blood velocity, wherein the vessel diameter is calculated as the difference between the measured blood vessel distension and an initial diameter ($D_0$) estimate; and
   displaying the calculated average blood pressure on an electronic display.

2. The method of claim 1, wherein the blood vessel is a pulmonary or systemic artery.

3. The method of claim 1, wherein the calculating includes determining the slope at the beginning of a cardiac cycle.

4. The method of claim 1, wherein the blood velocity measured is selected from centerline blood velocity and cross-sectional area average of the velocity.

5. The method of claim 1, wherein the Do is estimated with a selection from: a search algorithm, age-corrected allometric equations, diastolic diameter, clinically derived values, and an approximate based on patent history.

* * * * *